United States Patent [19]

Hanes et al.

[11] Patent Number: 4,767,574

[45] Date of Patent: Aug. 30, 1988

[54] CARBONYLATION OF ALLYLIC ETHERS TO ESTERS

[75] Inventors: Ronnie M. Hanes, Milford; Thomas S. Brima, Cincinnati, both of Ohio

[73] Assignee: National Distillers and Chemical Corporation, Cincinnati, Ohio

[21] Appl. No.: 783,884

[22] Filed: Oct. 3, 1985

[51] Int. Cl.$^4$ ............................................. C09F 5/08
[52] U.S. Cl. .................................... 260/410; 560/207
[58] Field of Search .................... 260/410 C; 560/207

[56] References Cited

U.S. PATENT DOCUMENTS

| | | | |
|---|---|---|---|
| 2,876,254 | 3/1959 | Jenner et al. | 560/114 |
| 3,161,672 | 12/1964 | Zachry et al. | 560/207 |
| 3,367,961 | 2/1968 | Brewbaker | 560/207 |
| 3,427,344 | 2/1969 | Tsuji et al. | 560/114 |
| 3,530,168 | 9/1970 | Biale | 560/207 |
| 3,626,005 | 12/1971 | Scheben et al. | 560/114 |
| 3,652,255 | 3/1972 | Oseika et al. | 71/98 |
| 4,055,721 | 10/1977 | Kawata et al. | 560/207 |
| 4,172,087 | 10/1979 | Knifton | 260/410.6 |
| 4,484,002 | 11/1984 | Lin | 562/519 |
| 4,519,956 | 5/1985 | Lin et al. | 562/519 |

OTHER PUBLICATIONS

Tsuji et al, *Journal of the American Chemical Society*, 86, pp. 4350–4353 (1964).

Primary Examiner—Charels F. Warren
Assistant Examiner—Elizabeth A. Hanley
Attorney, Agent, or Firm—Kenneth D. Tremain

[57] ABSTRACT

A method is disclosed for the production of esters by reaction of an allylic ether with carbon monoxide in the presence of a catalytically effective amount of a Group VIII noble metal catalyst and a halide compound to obtain esters. The halide compound is present in an amount sufficient to prevent the catalyst from being converted into a Group VIII metal during the reaction. When the reaction is conducted in the presence of a quaternary ammonium salt the ester may be extracted by solvent extraction to minimize catalyst decomposition caused when extractive distillation is used to separate the ester.

28 Claims, No Drawings

CARBONYLATION OF ALLYLIC ETHERS TO ESTERS

TECHNICAL FIELD

The present invention generally relates to the production of esters by the reaction of allylic ethers with carbon monoxide in the presence of a metal compound as a catalyst.

PRIOR ART

Palladium chloride has been employed as a catalyst for the carbonylation of alkoxyoctadienes to alkyl nonadienoate esters however only low yields (less than 10%) of the ester were produced. Compounds of the palladium-type metals (i.e. the Group VIII noble metals) therefore did not appear to be good candidates for catalyzing reactions of this type even though some catalytic activity was noted with palladium chloride. The production of esters in this type of reaction on an industrial scale would require higher yields than the 10% initially observed.

Scheben, U.S. Pat. No. 3,626,005 discloses a process for the preparation of unsaturated acyl halides by carbonylating vinylic halides in the presence of a Group VIII noble metal catalyst such as palladium metal, the catalyst composition optionally containing metals such as gold, silver, copper and the like. Additionally, Jenner, et al., U.S. Pat. No. 2,876,254 also disclose a process for the preparation of esters from olefins, carbon monoxide and alcohols in the presence of a catalyst system comprising a Group VIII noble metal such as palladium and an alcohol-soluble salt of tin or germanium.

Various other U.S. Patents similarly teach the production of esters such as Knifton, U.S. Pat. No. 4,172,087 in which a process for the preparation of unsaturated aliphatic esters from aliphatic dienes such as butadiene is disclosed by reacting such unsaturated components with carbon monoxide and an alcohol in the presence of a palladium catalyst and an amine base. Group VIII metal catalysts are also disclosed for the preparation of esters in a similar manner by Zachry, et al., U.S. Pat. No. 3,161,672; Tsuji, et al., U.S. Pat. No. 3,427,344; Fenton, U.S. Pat. No. 3,652,655; Biale, U.S. Pat. No. 3,530,168 and Brewbaker, U.S. Pat. No. 3,367,961.

Tsuji, et al. J.A.C.S. 86, pp. 4350-4353 (1964) discloses the carbonylation of allyl ethyl ether in ethanol as a solvent to ethyl 2-butenoate in the presence of palladium chloride as a catalyst, whereas Chan, XXIII International Conference on Coordination Chemistry, July 29August 3, 1984, Univ. of Colorado (Abstract of Poster Presentation TH p. 51-6) describes the affects of solvents, catalyst promoters and inhibitors on the palladium catalyst dicarbonylation of 1,4-difunctionalized-2-butenes.

None of the above references addresses the problem of overcoming the low selectivities obtained when employing a palladium halide catalyst for the production of esters by the reaction of allylic ethers with carbon monoxide.

Additionally, in the manufacture of alkyl acyclic esters using expensive Group VIII noble metal catalyst, it is necessary that the catalyst be recycled if it is to be employed on an industrial scale.

The ester product of the reaction may be separated from the reaction mixture by means of distillation, or vacuum distillation; however, both distillation processes require energy input which could also add to the cost of the process. Although solvent extraction processes are known in the art these known methods are not totally satisfactory for the separation of the ester from the catalyst either because of the cost of the solvents or the fact that some of the palladium catalyst is carried over into the ester that the catalyst is to be separated from.

SUMMARY OF THE INVENTION

Accordingly, it is an object of the present invention to overcome these and other difficulties encountered in the prior art.

It is a further object of the present invention to provide a catalyst for the reaction of an allylic ether with carbon monoxide for the production of an ester.

It is a further object of the invention to provide such a catalyst based on a Group VIII metal and especially a Group VIII metal halide.

It is an additional object of the present invention to provide a catalyst based on a Group VIII noble metal halide which is stable during the reaction of an allylic ether with carbon monoxide for the formation of an ester.

It is a further object of the present invention to provide a method for separating an ester from a catalyst comprising a Group VIII noble metal halide by means of a solvent extraction process.

These and other objects have been achieved according to the present invention which comprises a method for the production of esters comprising reacting an allylic ether with carbon monoxide in the presence of a catalytically effective amount of a catalyst to produce an ester, the catalyst comprising a Group VIII noble metal halide and mixtures thereof and a halide compound selected from the group of hydrogen halides, carbonyl halides, acyl halides and mixtures thereof. The halides in this respect comprise the chlorides, bromides and iodides.

The reaction is conducted by dissolving the catalyst in a solvent comprising a quaternary ammonium salt or phosphonium compound or mixtures thereof which are liquid at the reaction temperature and from which the alkyl acyclic ester produced is separated from the catalyst by solvent extraction with a non-polar organic solvent.

DETAILED DESCRIPTION

In the production of esters by the reaction of an allylic ether with carbon monoxide in the presence of a Group VIII noble metal catalyst (i.e. ruthenium, rhodium, palladium, osmium, iridium and platinum and mixtures thereof) such as a palladium chloride catalyst it was observed that although the palladium chloride did in fact catalyze the reaction to the ester, the yields of the ester obtained were less than 10%. In trying to determine the cause for these low yields which are unacceptable for industrial scale reactions it was noted that during the course of the reaction the palladium chloride catalyst was unstable in that the catalyst was being converted into palladium metal. Although the prior art would indicate that palladium metal would catalyze the reaction of carbon monoxide with an allylic ether actual experience established that the formation of palladium metal during the carbonylation reaction detracted from the activity of the catalyst.

Means were sought to prevent the catalyst from being converted into the metal during the course of the reaction whereupon it was discovered that by employing a halide compound selected from the group of hydrogen halides, carbonyl halides, acyl halides and mixtures thereof the instability of the Group VIII noble metal halides was overcome. The halides in this respect comprise the chlorides, bromides and iodides. Accordingly, the reaction is conducted in the presence of the Group VIII noble metal halide catalyst as described herein along with the halide compound which is present in an amount sufficient to prevent the catalyst from being converted into a Group VIII metal during the reaction.

The allylic ethers that may be reacted according to the method of the present invention comprise any acyclic or cyclic allylic ether having up to about 20 carbon atoms and especially those having from about 4 to about 20 carbon atoms. In addition, the aforesaid ethers may contain up to about 4 olefinically unsaturated positions and especially up to about 2 olefinically unsaturated positions along an acyclic hydrocarbon chain. The esters produced have up to about 21 carbon atoms and especially from 5 to about 21 carbon atoms and similarly may be acyclic or may comprise an acyclic ester group attached to a cyclic group such as a cyclic hydrocarbon and have up to about 4 olefinically unsaturated positions along the acyclic hydrocarbon chain and especially up to about 2 of such olefinically unsaturated positions. The acyclic hydrocarbon group of the ether or ester may be straight chain or a branched chain and has from 1 to about 6 and especially from 1 to about 4 carbon atoms.

Examples of various allylic ethers that may be reacted according to the method of the present invention comprises:
methyl allyl ether
8-methoxy-1,6-octadiene
methyl 2-butenyl ether
3-methoxy-1-phenylpropene
4-methoxy-1-phenyl-2-butene
methyl 4-methoxycrotonate
1-methoxy-2-penten-4-one
1,4-dimethoxy-2-butene
ethyl allyl ether
isopropyl allyl ether
8-isopropoxy-1,6-octadiene
1-ethoxy-2-hexene
3-ethoxy-1-phenylpropene
1-methoxy-2-hexene
1-isopropoxy-2-pentene
8-phenoxy-1,6-octadiene
phenyl allyl ether
benzyl allyl ether
1-phenoxy-2-butene
1-phenoxy-2-hexene
1-phenoxy-2-penten-4-one
1-phenoxy-2-pentene
benzyl 2-butenyl ether The catalyst employed for the carbonylation reaction of the present invention comprises the Group VIII noble metal halides, i.e., the halides of ruthenium, rhodium, palladium, osmium, iridium, platinum and mixtures thereof, ruthenium, rhodium, palladium and platinum being preferred and palladium being especially preferred. The halides are selected from chloride, bromide and iodide and mixtures thereof, the chloride being preferred.

The halide compounds that are employed in an amount sufficient to prevent the catalyst from being converted into a Group VIII metal during the reaction comprise hydrogen chloride, hydrogen bromide, hydrogen iodide, phosgene, acyl chlorides, acyl bromides, acyl iodides, and the like. Mixtures of these halide compounds may also be used. The acyl halides have from 1 to about 8 and especially 1 to about 5 carbon atoms and one or two halogen atoms such as acetyl chloride; acetyl bromide; acetyl iodide; proponyl chloride; butyryl chloride, malonyl chloride and the like. A lower alkanol (i.e. one having from 1 to about 6 carbon atoms) preferably is used with the carbonyl halide or acyl halide.

The catalyst is employed in the carbonylation reaction in an amount anywhere from about 0.005 mole % to about 1.0 mole % and especially from about 0.05 mole % to about 0.2 mole % based on the ether employed in the reaction, this amount comprising a catalytically effective amount.

The amount of the halide compound employed in the reaction may be anywhere from about 5 to about 50 molar excess and especially from about 10 to about 30 molar excess based on the Group VIII metal, this amount comprising an amount sufficient to prevent said catalyst from being converted into said Group VIII metal during the carbonylation reaction. Any other amount of catalyst or halide compound may be employed and is readily determined by a person having ordinary skill in the art knowing that the catalyst as described herein will promote the carbonylation reaction noted above and that the halide compound will prevent the Group VIII metal of the catalyst from being formed during the carbonylation reaction.

The carbonylation reaction may be conducted at temperatures from about 50° C. to about 200° C. and at pressures from about 1,000 psig to about 5,000 psig. Other temperatures and pressures may also be employed and may be readily determined by a person having ordinary skill in the art having the within disclosure of the catalyzed carbonylation reaction.

In another aspect of the invention, it has been discovered that the esters produced according to the invention may be separated from the catalyst by solvent extraction when the carbonylation reaction is conducted in the presence of a solvent comprising quaternary ammonium or phosphonium compounds such as the quaternary ammonium salts or mixtures thereof, and more particularly, the quaternary ammonium halides. Those quaternary ammonium salts that are liquid at the temperature of the carbonylation reaction are employed in this respect and generally comprise the tetra-alkyl ammonium halides especially the chlorides. Tetrabutyl ammonium chloride is especially suitable in this regard although other quaternary ammonium salts may be employed and include:
Tetrabutylammonium bromide
Tetra(decyl)ammonium bromide
Tetradodecylammonium bromide
Benzyldimethyltetradecylammonium chloride
Benzylhexadecyldimethylammonium chloride
Benzyldimethyldodecylammonium bromide
Benzyldimethyldodecylammonium chloride
Tetrahexylammonium chloride
Benzyltributylammonium chloride
Tetra(decyl)ammonium chloride Phosphonium compounds that may be employed comprise:
Tetrapentylphosphonium chloride Tetrahexylphosphonium chloride
Tetrabutylphosphonium chloride
Tetrabutylphosphonium bromide
Tetrabutylphosphonium iodide
Tetrahexylphosphonium bromide
Benzyltributylphosphonium chloride When the carbonylation reaction is conducted in the presence of a quaternary ammonium salt or phosphonium compound the ester obtained may be separated from the reaction mixture by means of solvent extraction whereby the ester is dissolved in a non-polar organic solvent such as a petroleum ether or the acyclic hydrocarbons and especially the aliphatic hydrocarbons having from about 4 to about 10 carbon atoms and especially those having from about 5 to about 8 carbon atoms. Either linear or branched chain acyclic hydrocarbon compounds may be employed in this respect although the linear ones are preferred. Examples of these hydrocarbons comprise pentane, hexane, heptane, octane, nonane and the like. Other solvents that may be employed comprise:

2-methyl pentane
2-methyl hexane
3-methyl hexane
2-methyl pentane
30–60 petroleum ether The following examples are illustrative.

EXAMPLE 1

Several reactions were conducted in 71 ml glass lined Parr-shaker bombs at 100° C., for six hours. In each of the four reactions, 5 ml (28.6 mmoles) of 8-methoxy-1,6-octadiene was charged to the Parr bomb followed by purging four times with CO after which the bomb was pressured to 2,000 psig with CO. The catalysts used in each instance comprise 0.005 g $PdCl_2$.

In the first bomb, 0.477 g $CuCl_2.2H_2O$ was charged; in the second bomb, 0.477 g $CuCl_2$. $2H_2O$, 0.25 ml 12.5% phosgene solution in toluene was charged; in the third bomb, 0.477 g $CuCl_2H_2O$ along with 17.9 ml acetyl chloride (0.5 mmole) was charged; and in the fourth bomb, 0.25 ml, 12.5% phosgene solution in toluene was also charged.

All reaction mixtures had small amounts of precipitate. The reaction products from each of the bombs was analyzed by GLC means employing a Silar 10 CP column and the conversion of 8-methoxy-1,6-octadiene and selectivity to methyl-3,8-nonadienoate was measured. The results obtained are listed below.

| | 8-Methoxy-1,6-octadiene | | Methyl-3,8-nonadienoate | |
|---|---|---|---|---|
| Bomb No. | Mmoles | Percent Conversion | Mmole | Percent Selectivity |
| 1 | 1.3 | 95.9 | 22.6 | 82.8 |
| 2 | 0.6 | 97.9 | 25.8 | 92.1 |
| 3 | 0.8 | 97.2 | 24.4 | 88.1 |
| 4 | 18.8 | 34.2 | 9.0 | 91.8 |

EXAMPLE 2

Four reactions were carried out in 71 ml glass lined Parr bombs. Each bomb was charged with 2.0 g tetrabutylammonium chloride solution in water (23% water) and 0.005 g $PdCl_2$. The bombs were dried at 90° C. in a vacuum oven (0.01 mm Hg) for four hours and let cool under vacuum overnight.

Each of the bombs was charged with 1 ml p-xylene (internal standard) 0.5 ml phosgene solution (12.5% in toluene) 5 ml 8-methoxy-1,6-octadiene (28.6 mmoles). Each of the bombs was charged with the following amounts of methanol: bomb 1; 0.030 ml methanol (0.74mmoles); bomb 2;0.060 ml methanol (1.5 mmoles); bomb 3; 0.119ml methanol (3.0 mmoles); bomb 4; 0.239 ml methanol (5.9 mmoles). The bombs were then purged four times with CO and pressured to 2,000 psig with CO and placed in a shaker oven at 100° C. for three hours.

When the reaction was complete, GLC analyses of the contents of each of the bombs was conducted to determine the conversion of the 8-methoxy-1,6-octadiene and the selectivity to methyl-3,8-nonadienoate. The results obtained are tabulated below.

| | 8-methoxy-1,6-octadiene | | Methyl,3-8,nonadienoate | |
|---|---|---|---|---|
| Bomb No. | Mmoles | Percent Conversion | Mmoles | Percent Selectivity |
| 1 | 14.7 | 48.6 | 12.9 | 92.8 |
| 2 | 6.9 | 75.9 | 19.1 | 88.0 |
| 3 | 3.8 | 86.7 | 20.8 | 83.4 |
| 4 | 0.2 | 99.3 | 25.3 | 89 |

The foregoing examples show that phosgene and a protic solvent such as a lower alkanol having 1 to 6 carbon atoms, e.g. methanol can be used to generate hydrogen chloride in bench-scale reactions. Conversion is dependent on the alkanol (e.g. methanol) charge even above the stoichiometric amount required to react with phosgene; selectivity is not significantly affected. Octadienyl chloride is formed in this reaction, its concentration increasing slowly to reach constant value.

Selectivities are not as high as expected in some runs. Therefore, the dependence of selectivity on ether conversion was determined. Selectivity increased with conversion to a maximum of 99% at 60% conversion, and decreased at higher conversions. This decrease resulted from further reaction of methyl nonadienoate to form ten-carbon dibasic esters.

The affect of phosgene concentration (in the range 0.02–0.08M) on reaction rate and ether selectivity was also explored. Rate, though not very sensitive to phosgene concentration in this range, was highest at about 0.05M phosgene. Maximum selectivities are also observed at this level (95% selectivity at 79% conversion; 99% selectivity at 44% conversion).

The affect of pressure in the range 500–3500 psig was also investigated. Maximum rate was observed at 2500 psig. Selectivity decreased from 97% to less than 90% above 3000 psig.

The foregoing data also indicate that in the carbonylation of 8-methoxy-1,6-octadiene to methyl-3,8-nonadienoate with palladium chloride as a catalyst the addition of a halide compound to the reaction solution stabilizes the palladium catalyst so that palladium does not precipitate out as a metal and high 8-methoxy-1,6-octadiene conversions may be realized.

The use of a quaternary ammonium salt as a solvent with the catalyst system allows removal of product ester (methyl-3,8-nonadieneate) by extraction with a non-polar organic solvent such as petroleum ether, pentane, hexane and the like. The soluble palladium catalyst, as illustrated in the examples may then be recycled without being exposed to a distillation step.

The esters obtained according to the method of the invention may be hydrogenated and used as lubricants, plasticizers or functional fluids or may be hydrolyzed to form an acid having unsaturated groups. The acid obtained may be incorporated into polyesters manufactured from phthalic anhydride, glycols, and maleic anhydride and which are subsequently cross-linked with styrene all of which is known in the art. The unsaturated acid obtained provides a site along the polyester chain for cross-linking with styrene or equivalent monomers.

Although the invention has been described by reference to some embodiments, it is not intended that the novel method for the production of esters by carbonylation of an alkyl acyclic ether in the presence of a catalyst be limited thereby but that modifications thereof are intended to be included as falling within the broad scope and spirit of the foregoing disclosure and the following claims.

What is claimed is:

1. A method for the production of esters comprising reacting an allylic ether with carbon monoxide to obtain an ester said reaction being conducted in the presence of a catalytically effective amount of a catalyst comprising a halide of a Group VIII noble metal and a halide compound selected from the group consisting of hydrogen halides, carbonyl halides, acyl halides and mixtures thereof said halide compound present in an amount sufficient to prevent said halide of a Group VIII noble metal from being converted into said Group VIII noble metal during said reaction.

2. The method of claim 1 where said allylic ether has from about 4 to about 20 carbon atoms and said ester has from about 5 to about 21 carbon atoms.

3. The method of claim 1 wherein said allylic ether comprises an alkoxy alkadiene and said ester comprises an alkyl alkadienoate.

4. The method of claim 1 where said Group VIII metal halide and said halide compound are selected from chloride, bromide or iodide and mixtures thereof.

5. The method of claim 4 where said Group VIII metal comprises a member selected from ruthenium, rhodium, palladium and platinum and mixtures thereof.

6. The method of claim 5 where said Group VIII metal comprises palladium and said halide compound comprises phosgene or hydrogen chloride.

7. The method of claim 5 where said halide compound comprises phosgene in combination with a lower alkanol.

8. The method of claim 5 where said halide compound comprises phosgene in combination with methanol.

9. The method of claim 5 where said allylic ether comprises a lower alkoxy alkadiene having from 4 carbon atoms to about 20 carbon atoms and said ester comprises a lower alkyl alkadienoate.

10. The method of claim 9 where said allylic ether comprises 8-methoxy-1,6-octadiene and said ester comprises methyl-3,8-nonadienoate.

11. The method of claim 5 where said reaction is conducted at temperatures from about 50° C. to about 200° C. and at pressures from about 1,000 psig to about 5,000 psig.

12. The method of claim 9 wherein said reaction is conducted at temperatures from about 50° C. to about 200° C. and at pressures of from about 1,000 psig to about 5,000 psig.

13. A method for the production of methyl nonadienoates comprising reacting methoxyoctadiene with carbon monoxide in the presence of a catalytically effective amount of a catalyst comprising a halide of a Group VIII noble metal and a halide compound selected from the group consisting of hydrogen halides, carbonyl halides, acyl halides and mixtures thereof, said halide compound present in an amount sufficient to prevent said halide of a Group VIII noble metal from being converted into said Group VIII noble metal during said reaction.

14. The method of claim 13 wherein said methoxyoctadiene comprises 8-methoxy-1,6-octadiene and said methyl nonaidenoate comprises methyl-3,8-nonadienoate.

15. The method of claim 13 where said Group VIII metal halide and said halide compound is selected from chloride, bromide or iodide and mixtures thereof.

16. The method of claim 15 wherein said Group VIII metal comprises a member selected from ruthenium, rhodium, palladium and platinum.

17. The method of claim 16 where said Group VIII metal comprises palladium and said halide compound comprises phosgene or hydrogen chloride.

18. The method of claim 16 where said halide comprises phosgene in combination with a lower alkanol.

19. The method of claim 16 where said halide compound comprises phosgene in combination with methanol.

20. The method of claim 17 where said reaction is conducted at temperatures of from about 50° to about 200° C. at pressures from about 1,000 psig to about 5,000 psig.

21. A method for the production of an ester comprising reacting an allylic ether with carbon monoxide to obtain an unsaturated ester said reaction conducted in the presence of a catalytically effective amount of a halide of a Group VIII noble metal and a halide compound selected from the group consisting of hydrogen halides, carbonyl halides, acyl halides and mixtures thereof in an amount sufficient to prevent said halide of a Group VIII noble metal from being converted into said Group VIII noble metal during said reaction, said catalyst dissolved in a solvent, liquid at the temperature of said reaction, selected from the group consisting of a quaternary ammonium salt, a phosphonium compound and mixtures thereof.

22. The method of claim 21 where said ester is separated from said catalyst by solvent extraction of said ester with a non-polar organic solvent.

23. The method of claim 22 where said quaternary ammonium salt comprises a tetraalkyl ammonium halide.

24. The method of claim 22 where said quaternary ammonium salt is tetrabutyl ammonium chloride and said solvent is selected from petroleum ether and acyclic hydrocarbons.

25. A method for the production of methyl nonadienoates comprising reacting methoxyoctadiene with carbon monoxide in the presene of a catalytically effective amount of a halide of a Group VIII noble metal and a halide compound selected from the group consisting of hydrogen halides, carbonyl halides, acyl halides and mixtures thereof, said halide compound present in an amount sufficient to prevent said halide of a Group VIII noble metal from being converted into said Group VIII noble metal during said reaction, said catalyst dissolved in a solvent of a quaternary ammonium salt that is liquid at the temperature of said reaction.

26. The method of claim 25 where said methyl nonadienoate is separated from said catalyst by solvent extraction of said methyl nondienoate with a non-polar organic solvent.

27. The method of claim 25 where said quaternary ammonium salt is a tetraalkyl ammonium halide.

28. The method of claim 27 wherein said quaternary ammonium salt is tetrabutyl ammonium chloride and said solvent is selected from petroleum ether and acyclic hydrocarbons.

* * * * *